United States Patent [19]

Godfrey Jr. et al.

[11] Patent Number: 4,720,585

[45] Date of Patent: Jan. 19, 1988

[54] AMINOPEPTIDASE INHIBITORS

[75] Inventors: Jollie D. Godfrey Jr., Trenton; Eric M. Gordon, Pennington, both of N.J.

[73] Assignee: E. R. Squibb & Sons, Inc.

[21] Appl. No.: 777,122

[22] Filed: Sep. 18, 1985

[51] Int. Cl.$^4$ ............... C07C 149/24; C07C 149/14
[52] U.S. Cl. ................... 564/340; 564/500; 564/501; 564/374; 564/389; 564/391; 564/440; 564/461; 546/312; 546/334; 548/337; 548/342; 548/483; 548/504; 549/68; 549/75; 549/480; 549/495
[58] Field of Search ........... 564/500, 501, 340, 324, 564/389, 391, 440, 461; 546/312, 334; 548/337, 342, 483, 504; 549/68, 75, 480, 495

[56] References Cited

PUBLICATIONS

Pickering, D. S. et al., "Structural Requirements for Specific Inhibition of Microsomal Aminopeptidase by Mercaptoamines", *Arch. Biochem. & Biophys.*, vol. 239, No. 2, Jun. 1985, pp. 368–374.

*Primary Examiner*—Anton H. Sutto
*Assistant Examiner*—John A. Sopp
*Attorney, Agent, or Firm*—Lawrence S. Levinson; Donald J. Barrack

[57] ABSTRACT

Aminopeptidase inhibitory activity is exhibited by compounds having the formula

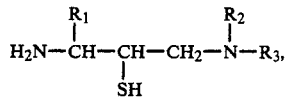

wherein $R_1$ is hydrogen, alkyl, carboxyalkyl, halo-substituted alkyl, hydroxyalkyl, aminoalkyl, mercaptoalkyl, alkylthioalkyl, (cycloalkyl)alkyl, (heteroaryl)alkyl, arylalkyl, carbamoylalkyl, guanidinylalkyl or heteroaryl; and $R_2$ and $R_3$ are each independently hydrogen, alkyl, cycloalkyl, hydroxyalkyl, aminoalkyl, aryl, arylalkyl, heteroaryl or heteroarylalkyl.

12 Claims, No Drawings

AMINOPEPTIDASE INHIBITORS

BRIEF DESCRIPTION OF THE INVENTION

Compounds having the formula

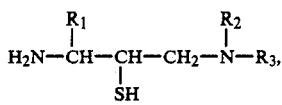

and pharmaceutically acceptable salts thereof, have aminopeptidase inhibitory activity, and can be used as analgesics. In formula I, and throughout the specification, the symbols are as defined below.

$R_1$ is hydrogen, alkyl, carboxyalkyl, halo-substituted alkyl, hydroxyalkyl, aminoalkyl, mercaptoalkyl, alkylthioalkyl, (cycloalkyl)alkyl, (heteroaryl)alkyl, arylalkyl, carbamoylalkyl, guanidinylalkyl or heteroaryl; and $R_2$ and $R_3$ are each independently hydrogen, alkyl, cycloalkyl, hydroxyalkyl, aminoalkyl, aryl, arylalkyl, heteroaryl or heteroarylalkyl.

Listed below are definitions of various terms used to describe the compounds of this invention. These definitions apply to the terms as they are used throughout the specification (unless they are otherwise limited in specific instances) either individually or as part of a larger group.

The terms "alkyl" and "alkoxy" refer to straight and branched chain groups having 1 to 7 carbon atoms.

The term "halo substituted alkyl" refers to alkyl groups in which one, or more, hydrogens have been replaced by chloro, bromo or fluoro groups. Exemplary groups are trifluoromethyl, which is preferred, pentafluoroethyl, 2,2,2-trichloroethyl, chloromethyl and bromomethyl.

The term "cycloalkyl" refers to cycloalkyl groups having 3, 4, 5, 6 or 7 carbon atoms.

The term "heteroaryl" refers to 2- or 3-furanyl, 2- or 3-thienyl, 2-, 3- or 4-pyridinyl, 4-imidazolyl and 3-indolyl.

The term "aryl", refers to phenyl and phenyl substituted with 1, 2 or 3 alkyl, alkoxy, alkylthio, hydroxy, chlorine, bromine, fluorine, amino, alkylamino, dialkylamino, nitro or trifluoromethyl groups.

DETAILED DESCRIPTION OF THE INVENTION

The compounds of formula I, and the pharmaceutically acceptable salts thereof, can be administered to a mammalian specie (e.g., humans) as an analgesic agent due to their ability to inhibit an enkephalin-degrading aminopeptidase.

It is well known that the weak and shortlasting analgesic activity of endogenous enkephalins can be attributed to their rapid inactivation. Enkephalins are metabolized by several hydrolytic enzymes present in the brain: (1) aminopeptidases release the Tyr[1] residue, (2) a dipeptidyl aminopeptidase releases the Tyr[1]-Gly[2] residue and (3) two enzymes cleave the penultimate Gly[3]-Phe[4] bond to release an intact dipeptide fragment, angiotensin-converting enzyme, and a discrete enzyme commonly designated enkephalinase.

It has been suggested that both enkephalinase and an aminopeptidase activity (probably membrane-bound) play key roles in enkephalin metabolism. The compounds of this invention inhibit the aminopeptidase activity and thus act as analgesic agents.

A compound of formula I, or a pharmaceutically acceptable salt thereof, can be administered to patients orally or parenterally in an effective amount within the daily dosage range of about 0.1 to about 25 milligrams of compound per kilogram of patient body weight. Administration can be once daily or in 2 to 4 divided daily doses.

The compounds of this invention can be prepared by coupling an aldehyde having the formula

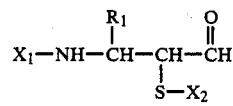

wherein $X_1$ is an amino protecting group (such as t-butoxycarbonyl or benzyloxycarbonyl) and $X_2$ is a sulfur protecting group (such as p-methoxybenzyl), with an amine having the formula $$HNR_2R_3 \qquad \qquad III$$

and chemically reducing the resulting compound (using, for example, sodium borohydride) to obtain the corresponding compound having the formula

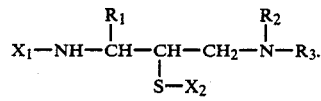

Deprotection of a compound of formula IV to obtain the corresponding product of formula I can be accomplished using art-recognized procedures. The particular deprotection reactions used will, of course, depend on the particular protecting groups present. If $R_2$ is hydrogen, it may be necessary to first protect the nitrogen atom to which the $R_2$ group is attached before deprotecting the sulfur atom.

The aldehyde reactant of formula II can be obtained by first treating an activated form (preferably a mixed anhydride) of an N-protected amino acid having the formula

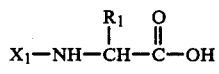

with diazomethane to yield a compound having the formula

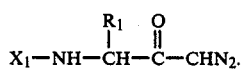

Treatment of a diazoketone of formula VI in methanol with silver benzoate and triethylamine yields a compound having the formula

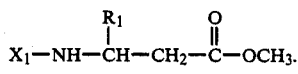

Treatment of a compound of formula VII with lithium diisopropylamide and a disulfide having the formula $$X_2-S-S-X_2 \quad \text{VIII}$$

at a reduced temperature yields the corresponding compound having the formula

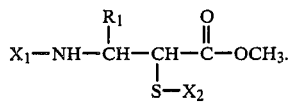

Reduction of the esterified carboxyl group of formula IX to the corresponding alcohol having the formula

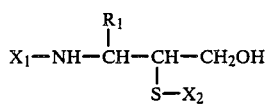

can be accomplished by treating a compound of formula IX with lithium chloride and sodium borohydride. Conversion of an alcohol of formula X to the corresponding aldehyde of formula II can be accomplished by treatment with sulfur trioxide pyridine complex and dimethylsulfoxide in the presence of diisopropylethylamine.

The compounds of formula I form acid-addition salts with a variety of inorganic and organic acids. The pharmaceutically acceptable salts include, for example, the hydrohalides, e.g., hydrochloride, hydrobromide, etc., sulfate, phosphate, nitrate, arylsulfonates, (e.g., camphorsulfonate, benzenesulfonate, toluenesulfonate, etc.), citrate, ascorbate, maleate, fumarate, pamoate, acetate, tartrate, salicylate and the like. It is frequently convenient to isolate the compound by forming the acid salt and precipitating in a medium in which it is insoluble.

In the compounds of formula I, the carbon atom to which the mercapto group is attached is asymmetric and the carbon atom to which the $R_1$ substituent is attached will also be asymmetric if $R_1$ is other than hydrogen. The compounds, therefore, may exist in stereoisomeric forms, and as racemic mixtures thereof. All of these are within the scope of this invention. The above-described syntheses can utilize the racemate or one of the diastereomers as the starting material. When the racemic starting material is used in the synthetic procedure, the stereoisomers obtained in the product can be separated by conventional chromatographic or fractional crystallization techniques.

The following examples are specific embodiments of this invention.

EXAMPLE 1

($\beta$S)-$\beta$-Amino-$\alpha$-[[(3-methylbutyl)amino]methyl]benzenepropanethiol, isomer A, hydrochloride (A) (S)-3-Diazo-2-oxo-1-(phenylmethyl)carbamic acid, 1,1-dimethylethyl ester To a solution of N-(t-butyloxycarbonyl)-L-phenylalanine (47.75 g, 0.18 mole) and N-methylmorpholine (19.8 ml, 0.18 mole) in dry tetrahydrofuran (300 ml) at −20° C. under argon was added over a 5 minute period isobutyl chloroformate (23.4 ml, 0.18 mole). After stirring for 20 minutes at −20° C., the N-methylmorpholine hydrochloride was removed by filtration and the filter cake was washed with a small portion of cold tetrahydrofuran. The filtrate was treated with a cold (0° C.), ethereal solution of diazomethane (~270 mmol, prepared from 64.2 g of Diazald and distilled). After stirring at 0° C. for 30 minutes, the mixture was warmed to room temperature. After stirring for 2.5 hours, the excess diazomethane was removed by bubbling a stream of argon through the reaction mixture for 1 hour. The bulk of the solvent was removed at reduced pressure and the residue was dissolved in ethyl acetate. The resulting solution was washed with water (twice), 0.25 M citric acid (twice), 1N sodium bicarbonate, and brine. After drying over anhydrous magnesium sulfate, the solvent was removed at reduced pressure and the residue was dissolved in isopropyl ether and placed in the cold (~5° C.). The resulting crystals were collected by filtration and washed with hexane to give (S)-3-diazo-2-oxo-1-(phenylmethyl)carbamic acid, 1,1-dimethylethyl ester as a bright yellow solid: 33.96 g, $R_f$0.21 (silica gel, hexane:ethyl acetate, 3:1). The mother liquors yielded an additional 7.45 g of (S)-3-diazo-2-oxo-1-(phenylmethyl)-carbamic acid, 1,1-dimethylethyl ester.

(B) (S)-3-[[(1,1-Dimethylethoxy)carbonyl]amino]benzenebutanoic acid, methyl ester To a solution of (S)-3-diazo-2-oxo-1-(phenylmethyl)-carbamic acid, 1,1-dimethylethyl ester (5.36 g, 18.52 mmol) in methanol (50 ml) was added 5.0 ml of a solution of silver benzoate (1.0 g) in triethylamine (10 ml). After nitrogen evolution had ceased, an additional 0.2 ml of the silver benzoate/triethylamine solution was added. After stirring for 15 minutes, the reaction mixture was treated with activated charcoal and filtered through Celite using ethyl acetate. The filtrate was concentrated at reduced pressure and the residue was dissolved in ethyl acetate and washed with water (twice), 1N sodium bicarbonate (twice), 1N hydrochloric acid (twice), 1N sodium bicarbonate and brine. After drying over anhydrous magnesium sulfate, the solvent was removed at reduced pressure and the residue chromatographed (flash, silica gel; benzene:isopropyl ether, 87.5:12.5) to give (S)-3-[(1,1-dimethylethoxy)carbonyl]amino]benzenebutanoic acid, methyl ester as a colorless solid: 4.33 g $[\alpha]_D^{20}=19.2°$ (c=1.06, methanol; $R_f$=0.33 (silica gel, benzene:ethyl acetate, 9:1).

(C) (3S)-3-[[(1,1-Dimethylethoxy)carbonyl]amino]-2-[[(4-methoxyphenyl)methyl]thio]benzenebutanoic acid, methyl ester To a solution of freshly distilled diisopropylamine (2.10 ml, 15 mmol) in anhydrous tetrahydrofuran (20 ml) at 0° C. under argon was added a hexane solution of n-butyl lithium (6.10 ml of a 2.40 M solution, 14.65 mmol). After stirring at 0° C. for 30 minutes, the resulting solution of lithium diisopropylamide was cooled to −78° C. and a solution of (S)-3-[[(1,1-dimethylethoxy)-carbonyl]amino]benzenebutanoic acid, methyl ester (2.0 g, 6.81 mmol) in dry tetrahydrofuran (8 ml) was added dropwise over a period of 5 minutes. After stirring at −78° C. for 15 minutes, a solution of p-methoxybenzyl disulfide (2.50 g, 8.18 mmol) in dry tetrahydrofuran (9 ml) was added. After 5 minutes at −78° C., the mixture was warmed to 0° C. and stirring continued for 45 minutes. The reaction was quenched with 1N hydrochloric acid and diluted with ethyl acetate. The resulting solution was washed with water, 1N hydrochloric acid, 1N sodium bicarbonate, and brine. After drying over anhydrous magensium sulfate, the solvent was removed at reduced pressure and the residue chromatographed (flash, silica; benzene: isopropyl ether, 92:8) to give (3S)-3-[[(1,1-dimethylethoxy)carbonyl]amino]-2-[[(4-methoxyphenyl)methyl]thio]benzenebutanoic acid, methyl ester as a colorless oil: 1.89 g, $R_f$=0.54 (silica gel, benzene:isopropyl ether, 4:1).

(D)
(1S)-[3-Hydroxy-2-[[(4-methoxyphenyl)methyl]thio]-1-(phenylmethyl)propyl]carbamic acid, 1,1-dimethylethyl ester To a solution of (3S)-3-[[(1,1-dimethylethoxy)carbonyl]amino]-2-[[(4-methoxphenyl)methyl]thio]benzenebutanoic acid, methyl ester (1.73 g, 3.88 mmol) in tetrahydrofuran (25 ml) and absolute ethanol (25 ml) was added lithium chloride (0.66 g, 15.6 mmol) and sodium borohydride (0.59 g, 15.6 mmol). After stirring at room temperature under argon for 24 hours, the mixture was quenched with 1N hydrochloric acid and diluted with ethyl acetate. The resulting solution was washed with water, 1N hydrochloric acid (twice), 1N sodium bicarbonate, and brine. After drying over anhydrous magnesium sulfate, the solvent was removed at reduced pressure and the residue chromatographed (flash, silica gel, benzene: acetone, 92:8) to give the separated diastereomers of (1S)-[3-hydroxy-2-[[(4-methoxyphenyl)methyl]thio]-1-(phenylmethyl)propyl]-carbamic acid, 1,1-dimethylethyl ester as colorless solids: Isomer A, 0.17 g, $R_f$=0.39, silica gel, benzene:ethyl acetate, 4:1).

(E)
(1S)-[3-Oxo-2-[[(4-methoxyphenyl)methyl]thio]1-(phenylmethyl)propyl]carbamic acid, 1,1-dimethylethyl ester A mixture of t-butanol (167 mg, 1.05 eq), 1,1,1-triacetoxy-2,1-benoxiodol-3(3H)-one (954 mg, 1.05 eq) and dry methylene chloride (8 ml) was stirred under argon at room temperature for 15 minutes. The mixture was then treated with a solution of (1S)-[3-hydroxy-2-[[(4-methoxyphenyl)methyl]thio]-1-(phenylmethyl)-propyl]carbamic acid, 1,1-dimethylethyl ester (890 mg, 2.14 mmol) and dichloromethane (8 ml). After stirring for 15 minutes, the reaction was diluted with ether and poured into 1N sodium bicarbonate containing a sevenfold excess of sodium thiosulfate (3.9 g, 15.75 mmol). The mixture was stirred until all solids dissolved. The layers were separated and the organic phase washed with 1N sodium bicarbonate, water and brine. Drying over anhydrous magnesium sulfate and removal of solvent yielded the title compound as a pale yellow solid: 860 mg (2.08 mmol); $R_f$=0.75 (silica gel, benzene: ethyl acetate, 4:1).

(F)
(1S)-[3-[[[(1,1-Dimethylethyl)oxy]carbonyl]amino]-2-(phenylmethyl)propyl]carbamic acid, 1,1-dimethylethyl ester, isomers A and B A mixture of (1S)-[3-oxo-2-[[(4-methoxyphenyl)methyl]thio]-1-(phenylmethyl)propyl]carbamic acid, 1,1-dimethylethyl ester (1.0 g, 2.4 mmol), isoamylamine (0.43 ml, 3 eq), crushed 3A sieves (1.5 g) and anhydrous benzene (10 ml) was stirred at room temperature under argon for 1.5 hours. The mixture was passed through a pad of Celite and concentrated. The concentrate was taken into icecold anhydrous methanol (10 ml) and while stirring in a 0° C. bath, treated with sodium borohydride (91 mg, 2 eq). After 45 minutes, the reaction was quenched with 1N hydrochloric acid, diluted with ethyl acetate and washed with water (twice), 1N hydrochloric acid (twice), 1N sodium bicarbonate and brine. Drying over anhydrous magnesium sulfate and removal of solvent yielded a yellow oil. The oil was taken into anhydrous tetrahydrofuran (10 ml) and treated with di-t-butyl-dicarbonate (340 mg, 1.3 eq) followed by diisopropylethylamine (0.3 ml, 1.3 eq). The resulting solution was stirred at room temperature under argon for two hours. The reaction was diluted with ethyl acetate and washed with 1N sodium bicarbonate, water and brine. Drying over anhydrous magnesium sulfate and removal of solvent yielded a mixture of diastereomers as a yellow oil. The oil was chromatographed three times (flash, silica gel LPS-1, hexane:ethyl acetate, 86:14) to partially separate the diastereomers. The mixture of diastereomers was chromatographed three times (flash, silica gel LPS-1, cyclohexane: ether, 4:1) to yield the separate diastereomers: isomer A, 430 mg (0.73 mmol); isomer B, 540 mg (0.92 mmol); $R_f$=0.24 isomer A, $R_f$=0.29 isomer B (silica gel, cyclohexane:ether, 4:1).

(G)
($\beta$S)-$\beta$-Amino-$\alpha$[[(3-methylbutyl)amino]methyl]benzenepropanethiol, isomer A, hydrochloride A solution of distilled trifluoroacetic acid (14 ml) and anisole (1 ml) was added to (1S)-[3-[[[(1,1-dimethylethyl)oxy]carbonyl]amino2-(phenylmethyl)propyl]carbamic acid, 1,1-dimethylethyl ester, isomer A (400 mg, 0.68 mmol) and stirred under argon at room temperature for 1 hour. The solution was cooled to 0° C. and treated with mercuric trifluoroacetate (320 mg, 1.1 eq). After one hour, the reaction was concentrated to a red oil. The oil was taken into a minimal amount of ether and hexane added to cause a precipitate to form. The solid was collected, washed with hexane and dried under argon to yield 550 mg of a grey solid. The solid was taken into 80% aqueous acetic acid (20 ml), and gassed with hydrogen sulfide for 20 minutes. The black reaction mixture was filtered through a pad of Celite then millipore (teflon). The filtrate was concentrated and the concentrate diluted with degassed double distilled water and 1N hydrochloric acid (2.04 ml, 1.5 eq). The resulting mixture was filtered (millipore, Metricel) and the clear, colorless filtrate lyophilized three times to yield the title compound as a colorless solid: 220 mg (0.65 mmol); $R_f$=0.62 (silica gel, butanol:acetic acid:water, 3:1:1), mass spectrum: $(M+H)^{+m/e}$=267; melting point 83.95° C.; $[\alpha]_D$=−42.4° (c=1.04, pyridine).

Analysis Calc'd. for $C_{15}H_{16}N_2S.2.12HCl.1.16H_2O$; C, 49.44; H, 8.35; N, 7.69; S, 8.80; SH, 9.07; Cl, 20.62, Found: C, 49.41; H, 8.11; N, 7.45; S, 8.63; SH, 8.89; Cl, 20.70.

EXAMPLE 2
($\beta$S)-$\beta$-Amino-$\alpha$a-[[(3-methylbutyl)amino]methyl]benzenepropanethiol, isomer B, hydrochloride A solution of distilled trifluoroacetic acid (14 ml) and anisole (1 ml) was added to (1S)-[3-[[[(1,1-dimethylethyl)oxy]carbonyl]amino]-2-[[(4-methoxyphenyl)methyl]thio]-1-(phenylmethyl)propyl]carbamic acid, 1,1-dimethylethyl ester, isomer B (450 mg, 0.767 mmol; see Example 1F) and stirred under argon at room temperature for one hour. The reaction was cooled to 0° C. and treated with mercuric trifluoroacetate (360 mg, 1.1 eq) for 1 hour after which it was concentrated to a red oil. The oil was taken into a minimal amount of ether and hexane was added to cause a precipitate to form. The solid was collected, washed with hexane and dried under argon to yield 550 mg of a grey solid. This material was taken into 80% aqueous acetic acid (20 ml) and gassed with hydrogen sulfide for 20 minutes. The black reaction mixture was filtered through a pad of Celite followed by millipore (teflon). The filtrate was concentrated and the concentrate treated with degassed double distilled water and 1N hydrochloric acid (2.3 ml, 1.5 eq). The resulting mixture was filtered (millipore, Metricel) and the clear, colorless filtrate lyophilized three times to yield the title compound as a colorless solid; 267 mg (0.79 mmol); $R_f$=0.62 (silica gel, butanol: acetic acid:water, 3:1:1); mass spectrum: $(M+H)^+ m/e$=267; melting point 108°–115° C.; $[\alpha]_D$= −26.93° (c=1.37, pyridine). Analysis Calc'd for $C_{15}H_{26}N_2S \cdot 2.07mHCl \cdot 0.58mH_2O$, mw=352.37:

C, 52.13; H, 8.36; N, 7.95; S, 9.10; SH, 9.38; Cl, 20.82, Found: C, 51.12; H, 8.24; N, 7.76; S, 8.91; SH, 8.12; Cl, 20.82.

EXAMPLE 3

($\beta$R)-$\beta$-Amino-$\alpha$-[[(3-methylbutyl)amino]methyl]benzenepropanethiol, isomer A, hydrochloride

(A) N-(t-Butoxycarbonyl)-D-phenylalanine

To a suspension of D-phenylalanine (33.0 g, 0.2 mol) in acetone (120 ml) and water (120 ml) was added triethylamine (41.8 ml, 1.5 eq) followed by 2-(t-butoxycarbonyloxyimino)-2-phenylacetonitrile (54.2 g, 1.1 eq). The resulting mixture was stirred overnight and then diluted with water (250 ml). The aqueous fraction was extracted twice with ether and the ether fractions were discarded. The aqueous fraction was acidified with 0.5M citric acid and extracted with ethyl acetate (2×500 ml). The ethyl acetate fractions were combined and washed with water and brine. After drying over anhydrous magnesium sulfate, the solvent was removed to give the title compound as a viscous yellow oil: 52.2 g.

(B) (R)-3-Diazo-2-oxo-1-(phenylmethyl)carbamic acid, 1,1-dimethylethyl ester To a solution of N-(t-butoxycarbonyl)-D-phenylalanine (52.2 g, 0.1986 mol) and N-methylmorpholine (21.6 ml, 0.196 mol) in anhydrous tetrahydrofuran (300 ml) at −20° C. under argon was added, over a period of 5 minutes, isobutylchloroformate (25.4 ml, 0.196 mol). After stirring at −20° C. for 20 minutes, the mixture was filtered and the filter cake was washed with a small portion of cold ether. The filtrate was treated with a cold (−20° C.), ethereal solution of diazomethane (~270 mmol, prepared from 64.2 g of Diazald and distilled). After stirring at −20° C. to 0° C. for 30 minutes, the mixture was warmed to room temperature. After stirring for 2 hours, the excess diazomethane was removed by bubbling a stream of argon through the reaction mixture for 45 minutes. The bulk of the solvent was removed at reduced pressure and the residue was dissolved in ethyl acetate. The resulting solution was washed with water (twice), 0.25 M citric acid (twice), 1N sodium bicarbonate, and brine. After drying over anhydrous magnesium sulfate, the solvent was removed at reduced pressure to give a bright yellow oil which was dissolved in isopropyl ether and placed in the cold (5° C.). After standing overnight, the resulting crystals were collected by filtration and washed with hexane to afford the title compound as a yellow solid: 20.3 g; $R_f$=0.29 (silica gel; hexane:ethyl acetate, 7:3); $[\alpha]_D^{20}$= +35.2° (c=2.56, methanol). The mother liquors yielded an additional 8.08 g of product.

(C) (R)-3-[[(1,1-Dimethylethoxy)carbonyl]amino]benzenebutanoic acid, methyl ester A solution of silver benzoate (1.0 g) and triethylamine (20 ml) was prepared. To a stirring mixture of (R)-3-diazo-2-oxo-1-(phenylmethyl)carbamic acid, 1,1-dimethylethyl ester (10.0 g, 34.56 mmol) and methanol (100 ml) was added a portion of the silver benzoate/triethylamine solution(10 ml). After 20 minutes additional silver benzoate/triethylamine was added (5 ml) and stirring continued for 45 minutes. The dark reaction mixture was treated with Celite, decolorizing carbon and brine. The resulting mixture was filtered through Celite and the filtrate concentrated, diluted with ethyl acetate and washed with water (twice), 1N sodium bicarbonate (twice), 1N hydrochloric acid (twice), 1N sodium bicarbonate and brine, dried over anhydrous magnesium sulfate and concentrated to an amber oil. The oil was chromatographed (flash, silica gel LPS-1, benzene:isopropyl ether 85:15) to yield a colorless oil. The oil was triturated with hexane to yield the title compound as a colorless solid: 8.43 g (28.7 mmol); $R_f$=0.26 (silica gel, benzene:isopropyl ether 85:15).

(D) (3R)-3-[[(1,1-Dimethylethoxy)carbonyl]amino]2-[[(4-methoxyphenyl)methyl]thio]benzenebutanoic acid, methyl ester To a 0° C. solution of diisopropylamine (2.1 ml, 15 mmol, 2.2 eq) and anhydrous tetrahydrofuran (20 ml) was added n-butyl lithium (6.0 ml, 14.65 mmol, 2.42M solution in hexane) and stirring continued for 30 minutes. The reaction was cooled to −78° C. and treated with a solution of (R)-3-[[(1,1-dimethylethoxy)carbonyl]amino]benzenebutanoic acid, methyl ester (2.0 g, 6.81 mmol) and tetrahydrofuran (8 ml). After 15 minutes, the mixture was warmed to −30° C., stirred 15 minutes and the orange solution treated with a solution of p-methoxybenzyl disulfide (2.5 g, 1.2 eq) and tetrahydrofuran (9 ml). After 5 minutes, the reaction was warmed to 0° C. and stirred for 45 minutes. The reaction was then quenched with the addition of 1N hydrochloric acid and diluted with ethyl acetate. The organic phase was washed with water, 1N hydrochloric acid, 1N sodium bicarbonate and brine, dried over anhydrous magnesium sulfate and concentrated to a yellow oil. The oil was chromatographed (flash, silica gel LPS-1, benzene:isopropyl ether 92:8) to yield the title compound as a yellow oil: 2.2 g (4.98 mmol).

(E) (1R)-[3-Hydroxy-2-[[(4-methoxyphenyl)methyl]thio]-1-(phenylmethyl)propyl]carbamic acid, 1,1-dimethylethyl ester A mixture of (3R)-3-[[(1,1-dimethylethoxy)carbonyl]amino]-2-[[(4-methoxyphenyl)methyl]thio]benzenebutanoic acid, methyl ester (2.2 g, 4.98 mmol), lithium chloride (9.08 mg, 4.3 eq), sodium borohydride (810 mg, 4.3 eq), absolute ethanol (20 ml) and anhydrous tetrahydrofuran (20 ml) was stirred at room temperature for 18 hours. The reaction was quenched with 1N hydrochloric acid, and diluted with ethyl acetate. The organic fraction was washed with water (twice), 1N hydrochlorice acid, 1N sodium bicarbonate and brine. Drying over anhydrous magnesium sulfate and removal of solvent yielded an oil. The oil was chromatographed (flash, silica gel LPS-1, benzene:acetone, 92:8) to yield the title compound as a mixture of diastereomers: 1.31 g (3.14 mmol); $R_f$=0.27 isomer A, $R_f$=0.20 isomer B (silica gel, benzene:acetone, 92:8).

(F)
(1R)-[3-Oxo-2-[[(4-methoxyphenyl)methyl]thio]-1-(phenylmethyl)propyl]carbamic acid, 1,1-dimethylethyl ester A mixture of t-butanol (193 mg, 1.05 eq), Dess-Martin periodinane (1.108 g, 1.05 eq) and anhydrous methylene chloride (16 ml) was stirred for 15 minutes. This mixture was treated with a solution of (1R)-[3-hydroxy-2-[(4-methoxyphenyl)methyl]thio]-1-(phenylmethyl)propyl]-carbamic acid, 1,1-dimethylethyl ester (1.04 g, 2.5 mmol) and methylene chloride (10 ml). After stirring for 20 minutes, the mixture was diluted with ether and poured into 1N sodium bicarbonate containing a sevenfold excess of sodium thiosulfate (4.3 g) and stirred until all solids dissolved. The layers were separated and the organic fraction washed with 1N sodium bicarbonate, water and brine. Drying over anhydrous magnesium sulfate and removal of solvent yielded the title compound as a pale yellow solid: 1.04 g (2.5 mmol); $R_f$=0.58 (silica gel, benzene:ethyl acetate, 4:1).

(G)
(1R)-[3-[[[(1,1-Dimethylethyl)oxy]carbonyl]amino]2-(phenylmethyl)propyl]carbamic acid, 1,1-dimethylethyl ester, isomers A and B A mixture of (1R)-[3-Oxo-2-[[(4-methoxyphenyl)methyl]thio]-1-(phenylmethyl)propyl]carbamic acid, 1,1-dimethylethyl ester (1.04 g, 2.5 mmol), isoamylamine (0.89 ml, 3 eq), crushed 3A sieves (2.5 g) and anhydrous benzene (15 ml) was stirred at room temperature under argon for two hours. The mixture was filtered through a pad of Celite and the filtrate concentrated to a yellow semisolid. This material was taken into ice-cold methanol (22 ml) and, while stirring at 0° C., treated with sodium borohydride (190 mg, 2 eq). After 30 minutes, the reaction was quenched with 1N hydrochloric acid, diluted with ethyl acetate and washed with water (twice), 1N hydrochloric acid (twice), 1N sodium bicarbonate and brine. Drying over anhydrous magnesium sulfate and removal of the solvent yielded a yellow oil. The oil was taken into anhydrous tetrahydrofuran (15 ml) and treated with di-t-butyl dicarbonate (709 mg, 1.3 eq) followed by diisopropylethylamine (0.57 ml, 1.3 eq). After 15 minutes, the reaction was diluted with ethyl acetate and washed with 1N sodium bicarbonate, water and brine. Drying over anhydrous magnesium sulfate and removal of solvent yielded a yellow oil. The oil was chromatographed four times (flash, silica gel LPS-1, cyclohexane:ether, 4:1) to yield isomer B: 700 mg (1.19 mmol). Fractions containing isomer A were combined and chromatographed (flash, silica gel LPS-1, cyclohexane:ether, 4:1) to yield 420 mg (0.72 mmol, 29%); $R_f$=0.33 isomer A, $R_f$=0.30 isomer B (silica gel benzene:isopropyl ether, 92:8).

(H)
($\beta$R)-$\beta$-Amino-$\alpha$-[[(3-methylbutyl)amino]methyl]benzenepropanethiol, isomer A, hydrochloride A solution of distilled trifluoroacetic acid (14 ml) and anisole (1 ml) was added to (1R)-[3[[[(1,1-dimethylethyl)oxy]carbonyl]amino]-2-(phenylmethyl)propyl]carbamic acid, 1,1-dimethylethyl ester, isomers A and B (400 mg, 0.68 mmol) and the resulting solution stirred for 1 hour. The reaction was cooled to 0° C. and treated with mercuric trifluoroacetate (338 mg, 1.1 eq) and stirred for 1 hour. The pink reaction was then concentrated to a red oil. The oil was taken into a minimal amount of ether and hexane was added to cause a precipitate to form. The solid was collected, washed with hexane and dried under argon to yield a grey solid. The solid was taken into 80% aqueous acetic acid (20 ml) and the solution gassed with hydrogen sulfide for 20 minutes. The black reaction mixture was filtered through Celite then millipore (teflon) and the filtrate concentrated. The concentrate was taken into double distilled degassed water and 1N hydrochloric acid (2.04 ml, 1.5 eq) and filtered (millipore, Metricel). The clear, colorless filtrate was lyophilized three times to yield the title compound as a brown solid: 210 mg (0.62 mmol); $R_f$=0.62 (silica gel, butanol:acetic acid:water, 3:1:1); mass spectrum: (M+H)+m/e=267; melting point 85°–102° C.; $[\alpha]_D$=44.70° (c=1.02, pyridine).

Analysis Calc'd for $C_{15}H_{26}N_2S \cdot 2.05mHCl \cdot 0.72mH_2O$, MW=354.16:

C, 50.87; H, 8.39; N, 7.91; S, 9.05; SH, 9.33; Cl, 20.52, Found: C, 50.88; H, 8.18; N, 7.79; S, 8.91; SH 9.10; Cl, 20.55.

EXAMPLE 4
($\beta$R)-$\beta$-Amino-$\alpha$-[[(3-methylbutyl)amino]methyl]benzenepropanethiol, isomer B, hydrochloride A solution of distilled trifluoroacetic acid (14 ml) and anisole (1 ml) was added to (1R)-[3-[[[(1,1-dimethylethyl)oxy]carbonyl]amino]-2-[[(4-methoxyphenyl)methyl]thio]-1-(phenylmethyl)propyl]carbamic acid, 1,1-dimethylethyl ester, isomer B (675 mg, 1.15 mmol; see example 3G) and the resulting solution stirred under argon at room temperature for one hour. This solution was cooled to 0° C. and treated with mercuric trifluoroacetate (540 mg, 1.1 eq) for 1 hour. The reaction was concentrated to a red oil and the oil taken into a minimal amount of ether. Hexane was added to cause the formation of precipitate. The solid was collected, washed with hexane and dried under argon to yield 810 mg of a nearly colorless solid. The solid was taken into 80% aqueous acetic acid (25 ml) and the solution gassed with hydrogen sulfide for 20 minutes. The black reaction mixture was filtered through Celite then millipore (teflon). The filtrate was concentrated and treated with degassed double distilled water and 1N hydrochloric acid (3.5 ml, 1.5 eq). The resulting mixture was filtered (millipore, Metricel). The clear, colorless filtrate was lyophilized three times to yield the title compound as a nearly colorless solid: 380 mg (1.12 mmol), $R_f$=0.62 (silica gel, butanol:acetic acid:water, 3:1:1); mass spectrum: (M+H)+m/e=267; melting point 114°–120° C.; $[\alpha]_D$=26.7° (c=1.13, pyridine).

Analysis Calc'd for $C_{15}H_{26}N_2S \cdot 2.05mHCl \cdot 0.55mH_2O$, MW 351.10.

C, 51.31; H, 8.37; N, 7.98; S, 9.13; SH, 9.42; Cl, 20.70, Found: C, 51,31; H, 8.61; N, 7.61; S, 8.87; SH, 9.22; Cl, 20.69.

EXAMPLE 5
(3S)-3-Amino-5-methyl-1-[(3-methylbutyl)amino]-2-hexanethiol, isomer A, hydrochloride Following the procedure of Example 3, parts B to H, but substituting N-(t-butoxycarbonyl)-L-leucine monohydrate for N-(t-butoxycarbonyl)-D-phenylalanine, yielded the title compound; $R_f=0.52$ (silica gel, butanol:acetic acid:water, 4:1:1); chemical ionization mass spectrum, $(M+H)^+m/e=233$; melting point 65° C. (shrinkage), 75°–80° C. (melting); $[\alpha]_D=+16.1°$ (c=0.52, pyridine), $[\alpha]_{365}=+55.8°$ (c=0.52, pyridine).

Analysis Calc'd. for $C_{12}H_{28}N_2S.2HCl.0.83mH_2O$, mw=320.22. C, 45.01; H, 9.96; N, 8.75; S, 10.01; Cl, 22.14; SH, 10.33, Found: C, 45.01; H, 9.54; N, 8.62; S, 9.95; Cl, 22.06; SH, 10.27.

EXAMPLE 6

(3S)-3-Amino-5-methyl-1-(3-methylbutyl)amino]-2-hexanethiol, isomer B, hydrochloride Following the procedure of Example 4, but substituting (3S)-[3-[[[(1,1-dimethylethyl)oxy]carbonyl]amino]-2-[[(4-methoxyphenyl)methyl]thio]-1-(2,2-dimethylethyl)propyl]carbamic acid, 1,1-dimethylethyl ester, isomer B (prepared in the procedure of Example 5) for (1R)-[3-[[[(1,1-dimethylethyl)oxy]carbonyl]amino]-2-[[(4-methoxyphenyl)methyl]thio]-1-(phenylmethyl)-propyl]carbamic acid, 1,1-dimethylethyl ester, isomer B, yielded the title compound; melting point 221° C. (dec); $[\alpha]_D=+2.04°$ (c=0.54, pyridine); chemical ionization mass spectrum, $(M+H)^+m/e=233$; $R_f=0.53$ (silica gel, butanol:acetic acid:water, 4:1:1).

Analysis Calc'd for $C_{12}H_{28}N_2S.2HCl.0.6mH_2O$: C, 45.59; H, 9.95; N, 8.86; S, 10.14; Cl, 22.43; SH, 10.46, Found: C, 45.65; H, 9.73; N, 8.50; S, 9.91; Cl, 22.31; SH, 10.11.

EXAMPLE 7

(3R)-3-Amino-5-methyl-1-[(3-methylbutyl)amino]-2-hexanethiol, isomer A, hydrochloride Following the procedure of Example 3, but substituting D-leucine for D-phenylalanine, yielded the title compound; $[\alpha]_D=-15.49°$ (c=0.51, pyridine); $[\alpha]_{365}=-56.08°$ (c=0.51, pyridine); chemical ionization mass spectrum, $(M+H)^+m/e=233$; $R_f=0.54$ (silica gel, butanol:acetic acid:water, 4:1:1).

Analysis Calc'd for $C_{12}H_{28}N_2S.HCl.0.85m H_2O$: C, 44.95; H, 9.96; N, 8.74; S, 10.00; Cl, 22.11; SH, 10.31, Found: C, 44.92; H, 9.62; N, 8.70; S, 9.99; Cl, 22.04; SH, 9.96.

EXAMPLE 8

(3R)-3-Amino-5-methyl-1-[(3-methylbutyl)amino]-2-hexanethiol, isomer B, hydrochloride Following the procedure of Example 4, but substituting (3R)-[3-[[[(1,1-dimethylethyl)oxy]carbonyl]amino]-2-[[(4-methoxyphenyl)methyl]thio]-1-(2,2-dimethylethyl)propyl]carbamic acid, 1,1-dimethylethyl ester, isomer B (proposed in the procedure of Example 7) for (1R)-[3-[[[(1,1-dimethylethyl)oxy]carbonyl]amino]-2-[[(4-methoxy-phenyl)methyl)propyl]carbamic acid, 1,1-dimethylethyl ester, isomer B, yielded the title compound, melting point 221° C. (dec.); $[\alpha]_D=-1.93°$ (c=0.57, pyridine); chemical ionization mass spectrum, $(M+H)^+m/e=233$; $R_f=0.55$ (silica gel, butanol:acetic acid:water, 4:1:1).

Analysis Calc'd for $C_{12}H_{28}N_2S.2HCl.0.5mH_2O$: C, 45.85; H, 9.94; N, 8.91; S, 10.20; Cl, 22.56; SH, 10.52, Found: C, 45.80; H, 9.76; N, 8.75; S, 9.99; Cl, 22.30; SH, 10.18.

Additional compound falling within the scope of this invention are compounds having the formula

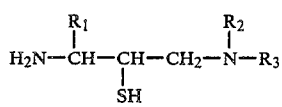

wherein the substituents are as defined below.

| | $R_1$ | $R_2$ | $R_3$ |
|---|---|---|---|
| 1. | $-CH_3$ | $-CH_2-CH(CH_3)_2$ | $-H$ |
| 2. | $-(CH_2)_4-NH_2$ | $-CH_2-CH(CH_3)_2$ | $-CH_3$ |
| 3. | $-(CH_2)_3-NH-\overset{NH}{\underset{\|\|}{C}}-NH_2$ | $-CH_2-\phantom{}\langle\text{phenyl}\rangle$ | $-H$ |
| 4. | $-CH_2-\langle\text{thiophene}\rangle$ | $-(CH_2)_4-NH_2$ | $-CH_3$ |
| 5. | $-CH_2-\langle\text{phenyl}\rangle$ | $-(CH_2)_4-NH_2$ | $-H$ |
| 6. | $-CH_2-\langle\text{phenyl}\rangle$ | $-(CH_2)_3-OH$ | $-H$ |
| 7. | $-CH_2OH$ | $-(CH_2)_3-NH-\overset{NH}{\underset{\|\|}{C}}-NH_2$ | $-H$ |

-continued

| | $R_1$ | $R_2$ | $R_3$ |
|---|---|---|---|
| 8. | $-(CH_2)_2-S-CH_3$ | $-CH_2-\phenyl$ | $-(CH_2)_2-OH$ |
| 9. | $-CH_2-\text{C}_6\text{H}_4-OH$ (para) | $-(CH_2)_3-NH_2$ | $-H$ |
| 10. | $-CH_2-\text{imidazole}$ | $-CH_2-\phenyl$ | $-CH_3$ |
| 11. | $-(CH_2)_2-\phenyl$ | $-CH_2-CH(CH_3)_2$ | $-H$ |
| 12. | $-CH_2-SH$ | $-CH_2-\phenyl$ | $-(CH_2)_2-OH$ |
| 13. | $-\underset{OH}{\overset{H}{C}}-CH_3$ | $-(CH_2)_2-OH$ | $-H$ |
| 14. | $-CH(CH_3)_2$ | $-(CH_2)_3-NH_2$ | $-H$ |
| 15. | $-CH_2-\text{indole}$ | $-CH_3$ | $-(CH_2)_4-NH_2$ |
| 16. | $-(CH_2)_3-NH_2$ | $-CH_2-\phenyl$ | $-H$ |
| 17. | $-CH_2-\text{C}_6\text{H}_4-OH$ (para) | $-CH_2-\phenyl$ | $-(CH_2)_4-NH_2$ |
| 18. | $-CH_2OH$ | $-CH_2-\phenyl$ | $-H$ |
| 19. | $-CH_2-\phenyl$ | $-CH_2-\underset{H}{\overset{CH_3}{C}}-OH$ | $-H$ |
| 20. | $-CH_3$ | $-(CH_2)_4-NH_2$ | $-H$ |

What is claimed is:

1. A compound having the formula $$H_2N-\underset{\underset{SH}{|}}{\overset{\overset{R_1}{|}}{CH}}-CH-CH_2-\overset{\overset{R_2}{|}}{N}-R_3,$$

or a pharmaceutically acceptable salt thereof, wherein
$R_1$ is phenylmethyl or 2-methylpropyl; and
$R_2$ and $R_3$ are each independently hydrogen, alkyl, cycloalkyl, hydroxyalkyl, aminoalkyl, aryl, arylalkyl, heteroaryl or heteroarylalkyl.

2. A compound in accordance with claim 1 wherein $R_1$ is phenylmethyl.

3. A compound in accordance with claim 1 wherein $R_2$ is hydrogen.

4. A compound in accordance with claim 1 wherein $R_3$ is alkyl.

5. A compound in accordance with claim 4 wherein $R_3$ is 3-methylbutyl.

6. A compound in accordance with claim 1 wherein $R_1$ is phenylmethyl, $R_2$ is hydrogen and $R_3$ is 3-methylbutyl.

7. A compound in accordance with claim 1 wherein $R_1$ is 2-methylpropyl.

8. A compound in accordance with claim 1 wherein $R_1$ is 2-methylpropyl, $R_2$ is hydrogen and $R_3$ is 3-methylbutyl.

9. The compound in accordance with claim 1, ($\beta$S)-$\beta$-amino-$\alpha$-[[(3-methylbutyl)amino]ethyl]benzenepropanethiol, or a pharmaceutically acceptable salt thereof.

10. The compound in accordance with claim 1, ($\beta$R)-$\beta$-amino-$\alpha$-[[(3-methylbutyl)amino]methyl]benzenepropanethiol, or a pharmaceutically acceptable salt thereof.

11. The compound in accordance with claim 1, (3S)-3-amino-5-methyl-1-[(3-methylbutyl)amino]-2-hexanethiol, or a pharmaceutically acceptable salt thereof.

12. The compound in accordance with claim 1, (3R)-3-amino-5-methyl-1-[(3-methylbutyl)amino]-2-hexanethiol, or a pharmaceutically acceptable salt thereof.

* * * * *

UNITED STATES PATENT AND TRADEMARK OFFICE
CERTIFICATE OF CORRECTION

PATENT NO. : 4,720,585

DATED : January 19, 1988

INVENTOR(S) : Jollie D. Godfrey, Jr.
Eric M. Gordon

It is certified that error appears in the above-identified patent and that said Letters Patent is hereby corrected as shown below:

Column 4, line 40, "(S)-3-[(1" should be --(S)-3-[[(1--.

Column 9, line 15, "[(4-" should be --[[(4- --.

Column 9, line 30, "amino]2-" should be --amino]-2- --.

Column 12, line 19, "methoxy-phenyl" should be --methoxyphenyl--.

Column 12, line 19, "methyl)" should be --methyl]--.

Column 12, line 19, after "methyl]" should be added --thio]-1-(phenylmethyl)--.

Column 16, line 5, "ethyl]" should be --methyl]--.

Signed and Sealed this

Seventh Day of March, 1989

*Attest:*

DONALD J. QUIGG

*Attesting Officer*  *Commissioner of Patents and Trademarks*